United States Patent [19]

Goet

[11] Patent Number: 4,944,410

[45] Date of Patent: Jul. 31, 1990

[54] HYGIENIC SUSPENSION FOR DENTAL OR MEDICAL INSTRUMENTS

[76] Inventor: Richard C. Goet, Prinseneiland 53, 2024 LM Amsterdam, Netherlands

[21] Appl. No.: 206,776

[22] Filed: Jun. 15, 1988

[30] Foreign Application Priority Data

Jun. 16, 1987 [NL] Netherlands ............... 8701398

[51] Int. Cl.⁵ .................................................. A61C 1/02
[52] U.S. Cl. ......................................................... 433/28
[58] Field of Search ....................... 433/33, 28, 77, 98, 433/99, 100

[56] References Cited

U.S. PATENT DOCUMENTS

| | | | |
|---|---|---|---|
| 3,727,658 | 4/1973 | Eldridge | 150/52 R |
| 3,776,387 | 12/1973 | Brent | 211/60 T |
| 3,991,473 | 11/1976 | Morgan | 251/63.4 |
| 4,340,368 | 7/1982 | Lococo | 433/28 |
| 4,561,540 | 12/1985 | Hunter et al. | 206/305 |
| 4,810,194 | 3/1989 | Snedden | 433/28 |

Primary Examiner—Cary E. Stone
Attorney, Agent, or Firm—Foley & Lardner, Schwartz, Jeffery, Schwaab, Mack, Blumenthal & Evans

[57] ABSTRACT

Hygienic suspension of an instrument for treatment connected to a dental or medical installation by means of an instrument tube, whereby the instrument tube comprises a magnetizable part, at least at the connection at the instrument, and a front panel of the installation comprises at least one magnet, the poles or pole shoes of which penetrate through the wall of the panel, serving for retaining the magnetizable part by attraction, and that a first insulating protection as a plastic casing or foil around the magnetizable part, and for the front panel, at least in the area of the magnet poles or pole shoes, a second insulating protection as a plastic foil are mounted removably, which are replaced after use of an instrument for a patient.

13 Claims, 1 Drawing Sheet

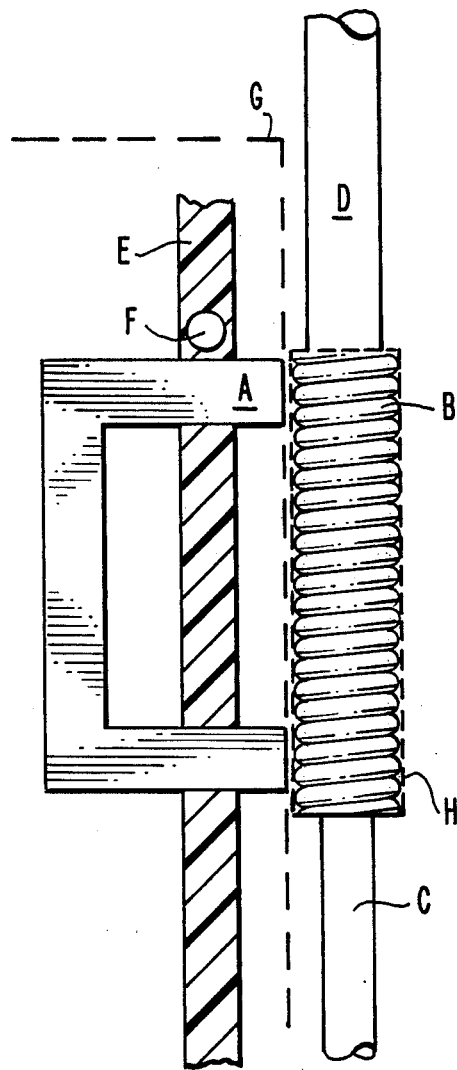

HYGIENIC SUSPENSION FOR DENTAL OR MEDICAL INSTRUMENTS

The invention relates to a hygienic suspension for an instrument for treatment connected by means of an instrument tube with a dental or medical installation.

Such instruments for treatment are applied in medical and in particular in dental practices. Examples of such instruments for treatment are dental drills, saliva suction-pipes, water-air guns and the like. Such instruments should be disinfected after use for a patient before they are used for a subsequent patient. Thereby arises the problem, that the instruments as such can be disinfected, for example in an autoclave, but the tubing, to which they are connected is not disinfected. In addition such instruments are in use time and again resuspended in installations, which can not be disinfected either. The latter installations comprise moreover often switches, which can not be disinfected either. The disinfection of apparatus, the use of disposables and wearing of gloves are only of relative value as long a tubing and suspension apparatus remain the sources of cross-infection. This is a growing problem in dentist practices amongst others as a consequence of the AIDS-virus.

It is now an object of the invention to provide a conclusive solution for this problem, which is easy to realize, is practical and can be carried out with little effort in current installations.

To that end the invention provides a hygienic suspension, as described in the introduction, characterized in that the instrument tube, at least at the connection to the instrument, comprises a magnetizable part, and a front panel of the installation comprises at least one magnet, the poles or pole shoes thereof, extending from the panel wall, serve for retaining by attraction the magnetizable part, and that a first insulating protection as a plastic casing or foil, and for the front panel, at least in the area of the magnet poles or pole shoes, a second insulating protection as a plastic foil are mounted removably, and which are replaced each time after use of the instrument for a patient By the suspension according to the invention the possibility is created in a simple manner, to insulate completely the non-autoclavable parts of the treatment apparatus, to wit the instrument tube and the front panel of the installation mutually by means of inexpensive plastic foil. Though this plastic foil may be contaminated during treatment of a patient, it can be replaced just simply by a new, clean foil after treatment of the patient, which latter foil does not require disinfection accordingly. The protected tube on the one hand and the front panel of the installation on the other hand remain decontaminated continuously.

In the invention the magnetizable part may be part of the instrument for treatment as such in specific cases, for example the handle of a drill or water-air gun. It is also possible to apply magnetizable rings, for example of steel, at that location. It is however also possible to have the magnetizable part consist of a casing which can be shoved over the tube. This casing may then consist effectively of a steel helical spring, which is sufficiently magnetizable to be attracted by a suitable magnet.

The magnet, which is positioned in the front panel of the installation is preferably a permanent magnet, so that the suspension mechanism can be effective at all times, and is not subject to possible failures in the power supply of the installation. The magnet can efficiently be like a U-magnet, mounted at the inner side of the front panel and with both poles passing through fitting holes in the front panel. Thus a proper mounting of the magent is obtained in a simple manner, whereby such a provision may be mounted with ease in an existing apparatus as well. According to a very effective embodiment the magnet is a cylindrical magnet, located at the inner side of the front panel against two pole shoes which pass through the panel wall. The advantage of this solution is, that the cylindrical magnet can be replaced with ease by a new magnet by simply withdrawing the old magnet and replacing by a new one. Particularly appropriate magnets are modern ceramic magnets, such as an anisotropic ferrox-dur magnet with pole plates.

In the embodiments described above use is made of two magnet poles or pole shoes for the suspension of an instrument against the front panel of an installation, but it will be obvious, that if required more poles or pole shoes can be used.

The invention further provides efficiently, that a switch is mounted in the vicinity of the magnet, which switches the instrument for treatment on or off respectively with taking off or resuspending respectively at the magnetic suspension. Though various possibilities are available thereby such as mechanical switches, infrared-detection switches etc. it is presently preferred to make use of a magnetically sensitive contact, mounted near one of the magnetic poles or pole shoes, and which will react to the change in magnetic flux as a consequence of removing or suspending the instrument. On suspending the instrument a closed magnetic circuit is obtained, whereby the outward flux is diminished. A switch reacting hereon can be for example an induction switch, Hall-effect switch etc.

A specifically effective solution was found to be the use of a reed-relay as the magnetically sensitive contact.

The invention will now be elucidated in detail with reference to the drawing, wherein an embodiment of the invention is shown in a diagrammatic manner.

In the drawing a permanent, open U-magnet is referred to with A, which forms the actual suspension mechanism together with a steel spring B. This spring B is shoved over an instrument tube C, which is connected to a dental instrument D, shown here only diagrammatically, above spring B, and which may be for example a drill, saliva suction-pipe, water gun or something similar.

The tube C is connected to the installation with its other extreme end, of which only the front panel E, made in plastic, is shown. Into this panel E is positioned the magnet A and that in such a way that the U-bend is at the inner side and both poles extend outwards through appropriate openings in the panel, in order that they can attract the steel spring B, if the latter is positioned against the poles. The mutual distance of the poles of magnet A is then suitably adjusted to the length of the steel helical spring B.

In addition a reed-relay F is present in the front panel E, taking care of activating the instrument D for treatment, when the closed magnetical circuit A-B is interrupted by removing spring B from magnet A. As a consequence thereof reed-relay F encounters a stronger magnetic field, that attracts the reed-contact, whereby the circuit for the feed current (not shown) is closed for instrument D and accordingly the latter is engaged. By returning B on the magnet A the reed-relay is again disconnected.

It is essential for the invention, that a plastic foil, G, diagrammatically shown in a broken line, is hanging over the front-panel E, insulating front-panel E with respect to instrument D, spring B and instrument tube C. In addition the instrument tube C and spring B showed over said tube C, are separately insulated by plastic foil H, so that during use neither front-panel E nor the instrument tube with spring B can be contaminated by sprayed saliva, blood or something similar. What may actually be contaminated are both plastic foils G and H, which are removed after treatment of a patient, and are replaced by new foils after disinfecting instrument D.

In the above the invention is illustrated by means of an example, presented diagrammatically. It will be obvious, that the invention is by no means limited to this example, but that numerous variations, modifications etc. are possible. In practice it is in many instances a matter of dental or medical installations with a number of instruments for treatment, connected thereto, and it will be obvious that such an installation, which is provided with a magnetic suspension as described in the above for each instrument for treatment, is fully within the scope of the present invention.

In addition the invention is suitable for any apparatus, whereby instruments, connected by means of tubing are used, and whereby the tubes and parts of the apparatus, with which the tubes come into contact, are difficult to disinfect.

For the magnetic system as well variations are possible. Thus instead of one magnet with two poles, pole shoes or pole plates respectively, use can be made of two or more pot magnets, for example samarium-cobalt pot magnets.

More variations and modifications will be obvious after having understood the above.

I claim:

1. A connection device for use with a treatment instrument, comprising:
    an elongated instrument tube having an instrument connecting end and a control connecting end;
    a magnetizable member disposed at said instrument connecting end;
    means for controlling the instrument, said control means having a first portion connected to said control connecting end of said instrument tube;
    a second portion of said control means including a magnetizing means disposed to magnetically interact with said magnetizable member thereby to control the operation of the instrument; and
    a replaceable means for covering said control means, said instrument tube and said magnetizable member, said covering means comprising at least one sheet which insulates said control means, said instrument tube and said magnetizable member from contamination.

2. The connection device according to claim 1, wherein said magnetizable member is a cylindrical casing disposed about said instrument tube.

3. The connection device according to claim 2, wherein said cylindrical casing is a helical steel spring.

4. The connection device according to claim 1, wherein said magnetizing means is a permanent magnet.

5. The connection device according to claim 4, wherein said permanent magnet is a U magnet, having both poles thereof extending beyond a front panel of said control means.

6. The connection device according to claim 4, wherein said permanent magnet is a cylindrical magnet positioned within a front panel of the control means and wherein two pole shoes penetrate said front panel and abut said permanent magnetic.

7. The connection device according to claim 1, wherein said magnetizing means is a ceramic magnet.

8. The connection device according to claim 1, wherein said magnetizing means includes at least one pot magent.

9. The connection device according to claim 1, wherein said control means further comprises a switch mounted within said control means in the vicinity of said magnetizing means, so that said switch operatively engages and disengages the instrument depending on the relative position of the magnetizable member and the magnetizing means.

10. The connection device according to claim 9, wherein said switch is mounted near a pole of said magnetizing means and is magnetically sensitive to react to the change in magnetic flux when said magnetizable member is brought near or removed from said magnetizing means.

11. The connection device according to claim 10, wherein said switch is a reed relay.

12. A treatment apparatus comprising:
    an treatment instrument;
    an elongated instrument tube connected to said treatment instrument at an instrument connecting end, said instrument tube having an opposite control connecting end;
    an magnetizable member disposed on one of said instrument connecting end and said treatment instrument;
    means for controlling said treatment instrument, said control means having a first portion connected to said control connecting end of said instrument tube;
    a second portion of said control means including a magnetizing means disposed to magnetically interact with said magnetizable member, thereby to control the operation of said instrument; and
    a replaceable means for covering at least said control means and said instrument tube, said covering means comprising at least one sheet which insulates said control means and said instrument tube from contamination.

13. The treatment apparatus according to claim 12, wherein said magnetizable member is formed on said treatment instrument.

* * * * *